United States Patent [19]

Bowman

[11] 4,291,701

[45] Sep. 29, 1981

[54] PRESSURE TRANSDUCING AND METHODS AND APPARATUS FOR FILLING A CAVITY

[75] Inventor: Ronald Bowman, Laguna Beach, Calif.

[73] Assignee: Bell & Howell Company, Chicago, Ill.

[21] Appl. No.: 923,600

[22] Filed: Jul. 11, 1978

[51] Int. Cl.³ .............................................. A61M 5/00
[52] U.S. Cl. ........................... 128/675; 128/214 E; 128/214 F; 73/756; 141/311 R
[58] Field of Search ............ 128/274, 213, 325, 214 F, 128/214 R, 214 E, 675; 141/311, 285; 73/706, 714, 756

[56] References Cited

U.S. PATENT DOCUMENTS

| | | | |
|---|---|---|---|
| 3,351,105 | 11/1967 | Perna | 141/131 X |
| 3,565,056 | 2/1971 | Stathan | 128/2 |
| 3,631,850 | 1/1972 | Levasseur | 128/2.05 R |
| 3,730,186 | 5/1973 | Edmund, Jr. et al. | 128/325 |
| 3,811,429 | 5/1974 | Fletcher et al. | 128/2.05 |
| 3,865,100 | 2/1975 | Kanai et al. | 128/2.05 D |
| 3,942,564 | 3/1976 | Nakazato | 141/311 R |
| 4,063,553 | 12/1977 | Karsh | 128/214 F |
| 4,063,555 | 12/1977 | Ulinder | 128/274 |

*Primary Examiner*—Henry K. Artis
*Attorney, Agent, or Firm*—Benoit Law Corporation

[57] ABSTRACT

Methods and apparatus for filling a cavity with a liquid from a hypodermic needle through a port provide the port with a straight passage leading to the cavity either directly or through a laterally offset further passage. The needle is partially inserted into the straight passage of the port. The partially inserted needle is stopped by engagement inside the port short of the cavity while an overflow and gas escape path is provided through the straight passage along the outside of the stopped partially inserted needle.

28 Claims, 7 Drawing Figures

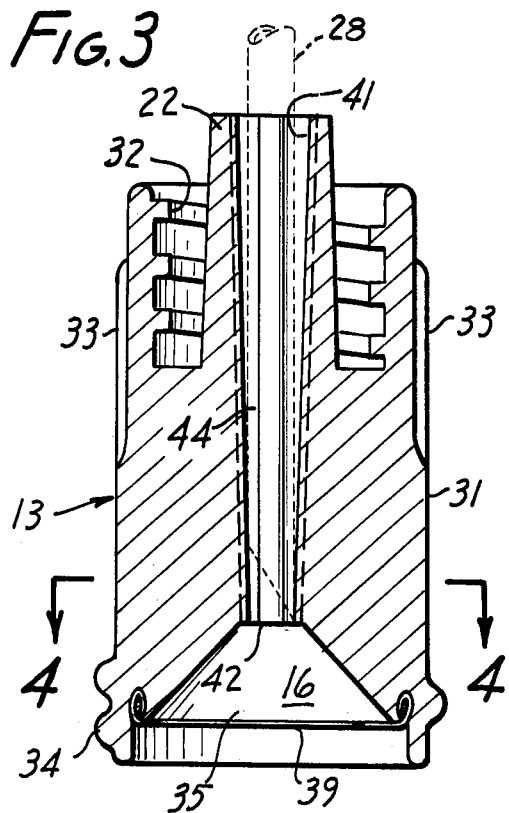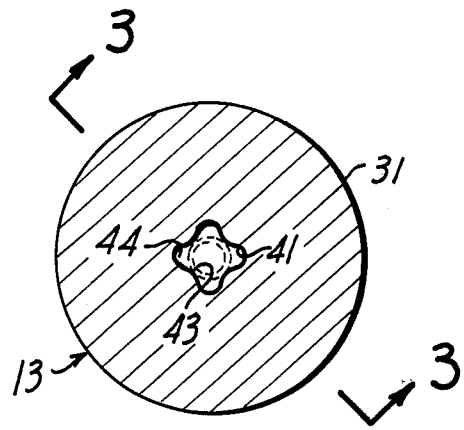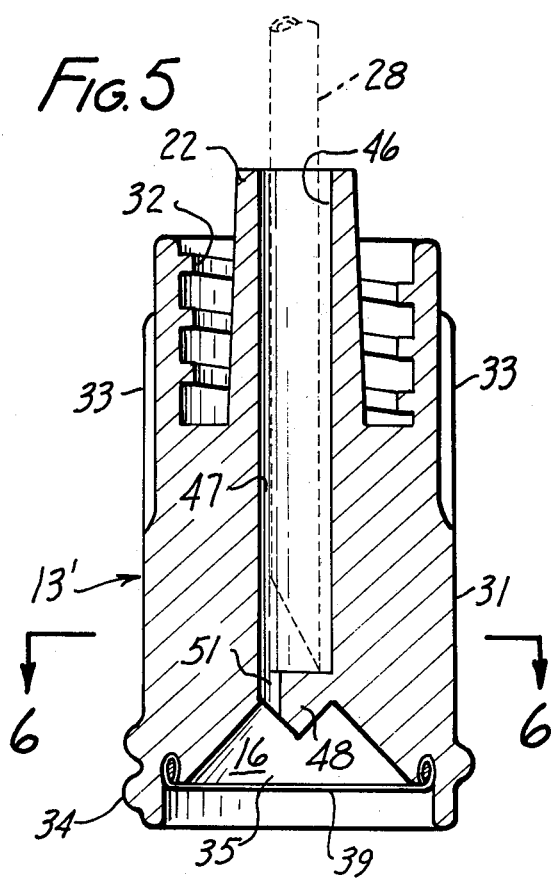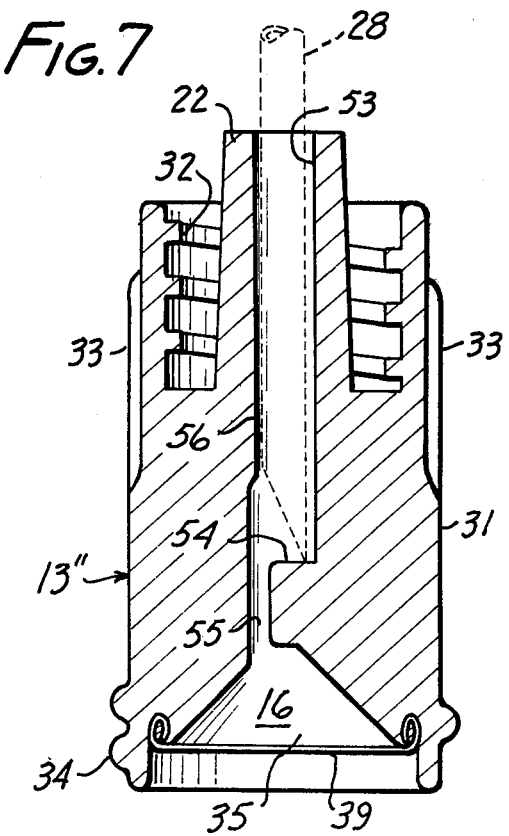

PRESSURE TRANSDUCING AND METHODS AND APPARATUS FOR FILLING A CAVITY

BACKGROUND OF THE INVENTION

1. Field of the Invention

The subject invention relates to methods and apparatus for filling a cavity with a liquid through a hypodermic needle and also to pressure transducing and pressure transducers, and domes for pressure transducers.

2. Prior-Art Statement

The prior art, like the subject invention, are herein primarily described in terms of physiological pressure transducers, although the scope of the subject invention obviously is not limited to such devices.

As apparent from U.S. Pat. No. 4,063,553 domes for physiological pressure transducers are typically provided with two ports; the second port facilitating filling of the internal dome cavity with saline solution, or other liquid, and the removal of all air bubbles after the dome has been installed on the transducer. For miniature transducers, it is generally desirable to use domes with a single, preferably coaxial port.

Since filling such domes is difficult after installation, they are frequently filled from the open end prior to attachment to the transducer. Typically, a syringe with a hypodermic needle is used for this purpose.

Such a procedure is awkward and untidy for reusable domes and impossible for domes with isolation membranes which could be pierced by the hypodermic needle.

Several patents located in the course of a novelty search have been considered, and found devoid of a solution of the above mentioned problem.

For instance, U.S. Pat. No. 3,565,056 provides a permanently attached conduit for supplying a saline solution to the chamber and internal parts of a strain-gage sensor assembly and catheter during pressure measurements. U.S. Pat. No. 3,631,850 proposes the use of a valve for filling the interior chamber and the bores of a transducer with a pressure-transmitting liquid. U.S. Pat. No. 3,811,429 proposes the use of a hypodermic needle or filling a cavity at a pressure transducer with a liquid. In particular, that patent proposes an internally threaded port into which a closing screw may be inserted, and a channel extending between that port and the transducer cavity at an angle to the internally threaded port. For the placement of a liquid into the transducer cavity, it is proposed to remove the screw and to insert a hypodermic needle or the like into contact with the obliquely extending channel defining the filling port. In practice, air or other gases may be entrapped in or at the cavity in such a structure and difficulties are encountered in actually transferring the injected liquid from the threaded port to the obliquely extending channel and hence to the transducer cavity.

U.S. Pat. No. 3,865,100 proposes the use of two ports, one for attachment to an injection syringe or catheter and the other, extending laterally into the transducer, for the supply of a physiological saline solution to the transducer cavity.

Reference may also be had to U.S. Pat. Nos. 3,157,201, 3,623,479, 3,731,680, 3,807,142, and 3,996,027, which have been cited in connection with the above mentioned U.S. Pat. No. 4,063,553, but are not considered particular pertinent in the present context.

SUMMARY OF THE INVENTION

It is a general object of this invention to overcome the above mentioned disadvantages and satisfy the above mentioned needs.

It is a related object of this invention to provide improved methods of filling a cavity and a port with a liquid through a hypodermic needle.

It is a germane object of this invention to provide improved apparatus having a port and a cavity for receiving a liquid from a hypodermic needle through such port.

It is also an object of this invention to provide improved domes for pressure transducers.

It is also an object of this invention to provide improved physiological pressure transducer systems.

Other objects of the invention will become apparent in the further course of this disclosure.

From one aspect thereof, the subject invention resides in a method of filling a cavity and a port extending for a distance from the cavity with a liquid through a hypodermic needle longer than that distance, while permitting gas and excess liquid to escape. According to this aspect, the invention resides, more specifically, in the steps of providing the port with a straight passage leading into the cavity, partially inserting the needle into the straight passage of the port, stopping the partially inserted needle by engagement inside the port short of the cavity while providing an overflow and gas escape path throughout the straight passage along the outside of the stopped partially inserted needle, injecting liquid through the needle into the cavity while preserving the overflow and gas escape path, and withdrawing the needle from the port while continuing to inject liquid through the needle until the port is filled with the liquid.

A method according to a similar aspect of the subject invention comprises the steps of providing the port with a straight first passage having a larger diameter than the needle and a bottom portion spaced from the cavity, and with a second passage extending between the first passage and the cavity in the same direction as the first passage, partially inserting the needle into the first passage, stopping the partially inserted needle with the bottom portion while providing an overflow and gas escape path through the first passage along the outside of the stopped partially inserted needle, injecting liquid through the needle and second passage into the cavity while preserving the overflow and gas escape path, and withdrawing the needle from the port while continuing to inject liquid through the needle until the port is filled with the liquid.

From another aspect thereof, the invention resides in an apparatus having a port and a cavity for receiving a liquid from a hypodermic needle through the port, comprising in combination a straight passage in the port leading to the cavity for receiving part of the needle, means in the port for engaging the needle inside the port and stopping the needle short of the cavity, and means in the port for providing an overflow and gas escape path throughout the straight passage.

According to another aspect thereof, the invention resides in an apparatus having a port and a cavity for receiving a liquid from a hypodermic needle through the port, comprising a tapered passage in the port extending in the direction of the cavity, having a minor diameter smaller than the outside diameter of the hypodermic needle whereby the needle is stopped short of the cavity, and having an overflow and gas escape path throughout the port.

From another aspect thereof, the invention resides in an apparatus having a port and a cavity for receiving a liquid from a hypodermic needle through the port, comprising in combination a straight first passage in the port having a larger diameter than the needle and a bottom portion spaced from the cavity for stopping the needle short of the cavity, and a second passage extending between the first passage and the cavity in the same direction as the first passage.

From another aspect thereof, the invention resides in a dome for pressure transducer having a port, a cavity for receiving a liquid from a hypodermic needle through the port, and an opening for a transduction of pressure variations relative to the cavity, comprising in combination an isolation membrane closing the opening for the liquid, a straight passage in the port leading to the cavity for receiving part of the needle, means in the port for engaging the needle inside the port and stopping the needle short of the cavity, and means in the port for providing an overflow and gas escape path throughout the straight passage.

A dome according to a similar aspect of the invention comprises in combination an isolation membrane closing the opening for the liquid, a tapered passage in the port extending in the direction of the cavity, having a minor diameter smaller than the outside diameter of the hypodermic needle whereby the needle is stopped short of the cavity, and having an overflow and gas escape path throughout the port.

A dome according to another similar aspect of the invention comprises in combination an isolation membrane closing the opening for the liquid, a straight first passage in the port having a larger diameter than the needle and a bottom portion spaced from the cavity for stopping the needle short of the cavity, and a second passage extending between the first passage and the cavity in the same direction as the first passage.

BRIEF DESCRIPTION OF THE DRAWINGS

The subject invention and its objects and aspects will become more readily apparent from the following detailed description of preferred embodiments thereof, illustrated by way of example in the accompanying drawings, in which like reference numerals designate like or functionally equivalent parts, and in which:

FIG. 3 is a longitudinal section, on an enlarged scale, through a pressure transducer dome in accordance with a preferred embodiment of the subject invention, and useful in the system of FIG. 1;

FIG. 4 is a section along the line 4—4 of FIG. 3;

FIG. 5 is a view, similar to FIG. 3, of a pressure transducer dome in accordance with a further preferred embodiment of the subject invention;

FIG. 7 is a view similar to FIGS. 3 and 5 of a pressure transducer dome in accordance with yet another preferred embodiment of the subject invention.

DESCRIPTION OF PREFERRED EMBODIMENTS

Figure 1:
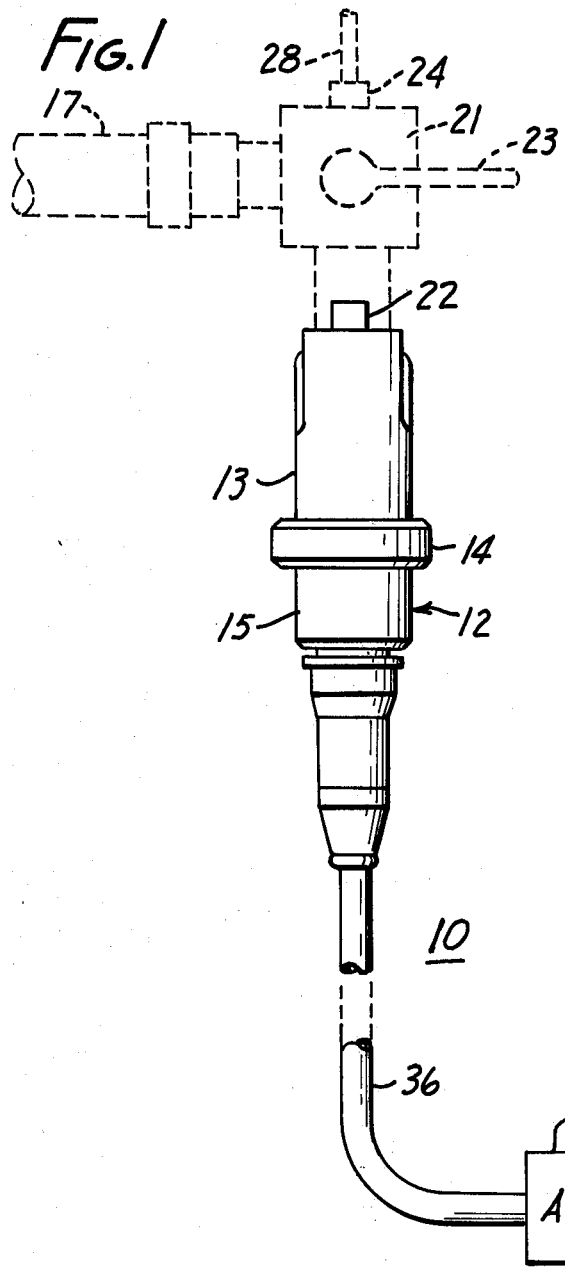
FIG. 1 is an elevation of part of a blood pressure transducing system embodying the subject invention.

The physiological or blood pressure transducing system 10 shown in FIG. 1 has a blood pressure transducer 12 provided with a transparent dome 13 of glass or a suitable plastic. The dome 13 is threaded into a circular nut 14 on the transducer body 15.

In practice, pressure signals are transferred to a cavity 16 in the dome (see FIGS. 3, 5 and 7) from a living organism via a compatible or physiological solution in a catheter 17 which is connected to a shutoff valve 21 releasably connected to the dome structure 13 and communicating with a single inlet port 22 thereof. By way of example, the valve 21 may be manually actuable via a handle 23 between a first position in which the dome cavity is vented to atmosphere through the port 22 and a valve outlet 24, with the catheter 17 being then blocked off, and an alternative second position in which the valve outlet 24 is blocked off and the catheter 17 connected to the dome cavity via the port 22.

Depending on the nature and condition of the living organism and the purpose to be accomplished, the compatible or physiological liquid 26 used in the pressure transducer system may, for instance, be a saline or dextrose solution which may be administered by a syringe 27 via a hypodermic needle 28. The syringe has a piston 29 by means of which the requisite liquid may be ejected through the needle 28.

If desired, and as indicated in FIG. 1, the needle 28 may be partially inserted into the transducer dome inlet port 22 via the valve 21 when in its open position in which the valve port 24 is connected through to the transducer dome port 22.

Figure 2:
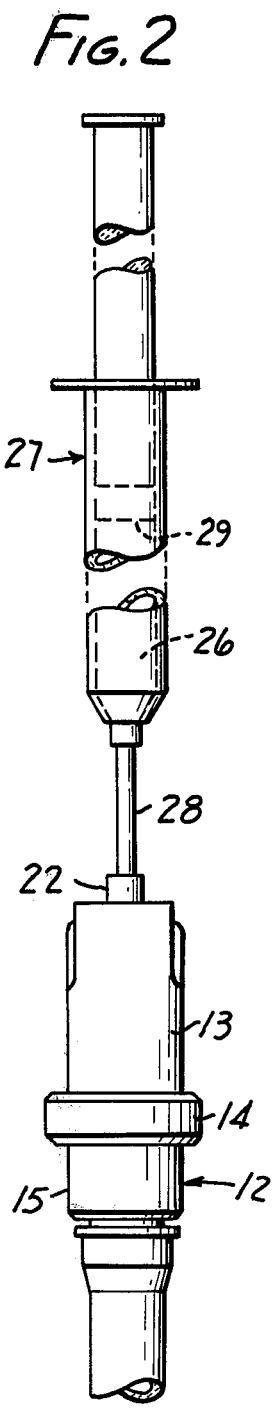
FIG. 2 is a view similar to FIG. 1 showing the filling of a blood pressure transducer dome with a physiological liquid in accordance with a preferred embodiment of the subject invention.

Alternatively, and as shown in FIG. 2, the needle 24 may be partially inserted into the port 22 prior to application of the valve 21 with catheter 17 to the transducer dome 13.

As seen in the drawings, the transducer domes herein shown may have several conventional features. For instance, each transducer dome may have a dome body or structure 31 equipped with a fitting 32 for releasable attachment of the catheter or valve structure to the transducer dome. In this respect, while a Luer fitting has been shown, a Linden or other fitting may be used instead. The dome structure has fluted portions or ribs 33 which facilitate manual engagement of the transducer dome during attachment and removal of the catheter system.

The dome structure 31 has a threaded portion 34 around the dome cavity 16 for engagement by the transducer nut 14.

The dome has an opening 35 for a transduction of pressure variations relative to the cavity 16. For instance, blood or other pressure variations in the liquid in the cavity 16 may be transferred to the transducer 12 for generation of electrical pressure signals which are applied via a cable 36 to an electronic amplifier 37 and other pressure monitoring or indicating equipment.

Alternatively, it is possible to apply alternating electric signals to the transducer and to transduct resulting pressure variations to the liquid in the cavity 16 where such is desired in a utilization of the principles of the subject invention.

The domes herein disclosed may be reusable or disposable, as desired or expedient for a given application.

In particular, the transducer domes shown in FIGS. 3 to 7 are equipped with an isolation membrane 39 which spans the dome cavity opening 35. The isolation membrane 39 closes the opening 35 for the liquid in the cavity 16, but not for the pressure variations which are transduced relative to that liquid. The isolation membrane 39 may be made of a thin plastic or other flexible material.

As shown in FIG. 2, liquid may be administered to the dome 13 through the hypodermic needle while the dome is installed on the transducer 12. However, it is often preferable in practice in terms of air bubble removal and operational convenience to administer the liquid through the needle 28 preparatory to installation of the dome on the transducer 12. The isolation membrane 39 renders such a procedure feasible.

However, absent implementation of the subject invention in the transducer dome, the isolation membrane 39, being located opposite the inlet port 22, could easily be pierced by the hypodermic needle 28 when traversing the cavity 16. Similarly, the transducer 12 and particularly its transducer membrane could be damaged by the inserted hypodermic needle 28.

Theoretically, one could contemplate manufacturing and supplying hypodermic needles for the syringe 27 that are shorter than the length of the inlet port so that they can never penetrate the dome cavity 16.

However, such a special manufacture and supply would not only be impractical but would not effectively preclude the use of regular, longer hypodermic needles by the operator of the equipment.

To overcome this problem and to satisfy the above mentioned need, the subject invention stops a partially inserted needle short of the cavity 16 by engagement inside the port 22 while providing an overflow and gas escape path through an at least essentially straight passage without resorting to angled or contorted port passage arrangements.

Thus, in accordance with a preferred embodiment of the subject invention shown in FIGS. 3 and 4, the dome 13 is provided with a tapered passage 41 in the port 22. As apparent in FIG. 3, the taper of the passage 14 extends in the direction of the cavity 16 and has a minor diameter 42 at the cavity 16 smaller than the outside diameter of the hypodermic needle 28.

In this manner, the needle 28 becomes stuck in the port 22 and cannot proceed to the cavity 16. In other words, the needle 28 is stopped short of the cavity 16 by engagement with wall portions of the tapered passage 41.

As shown in FIGS. 3 and 4, the tapered passage 41 is fluted, being provided with projecting ribs 43 and having corresponding straight overflow and gas escape passages or paths 44 throughout the port 22.

Hypodermic needles of regular length, or of any length, can thus be used at 28 and inserted into the port 22 in the practice of the subject invention.

Considering now the invention in terms of its methods, it is seen that the invention, according to a preferred embodiment thereof, resides in a method of filling a cavity 16 and a port 22 extending for a distance from the cavity with a liquid through a hypodermic needle 28 longer than that distance, while permitting gas and excess liquid to escape.

The invention according to this preferred embodiment resides in the steps of providing the port with a straight passage 41 leading to the cavity 16, partially inserting the needle 28 into that straight passage of the port 22, stopping the partially inserted needle by engagement inside the port short of the cavity 16 while providing at least one overflow and gas escape path 44 throughout the straight passage 41 along the outside of the stopped, partially inserted needle 28, and injecting liquid through the needle into the cavity while preserving the overflow and gas escape path 44. The syringe 27 is then lifted away from the dome 13 whereby the needle 28 is withdrawn from the port 22. However, during such withdrawal the operator continues by relative depression of the piston 29 to inject liquid through the needle 28 until the port is filled with the liquid and all air or gas bubbles and spaces are removed. The liquid then forms a meniscus on top of the port 22 facilitating a gas-bubble free attachment of the catheter system to the transducer dome.

In FIG. 3, the partially inserted hypodermic needle 28 is stopped in the port 22 short of the cavity 16 or minor diameter 42 by engagement with a wall portion of the tapered straight passage 41.

It may thus be said broadly that the partially inserted needle 28 is stopped by a partial obstruction which permits passage of liquid from the port 22 to the cavity 16, but which stops the partially inserted needle short of that cavity. This is also the case in the embodiment shown in FIGS. 5 to 7.

In particular, the dome 13' of FIG. 5 also has a straight passage 46 in the port which provides for an overflow and gas escape path 47 throughout the straight passage along the outside of the stopped, partially inserted needle 28.

Figure 6:
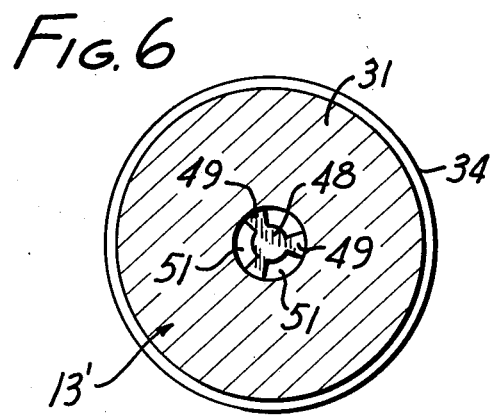
FIG. 6 is a section along the line 6—6 of FIG. 5.

In the embodiment of FIG. 5, the partially inserted needle 28 is stopped short of the cavity 16 by an obstruction 48 which, as seen in FIG. 6, is centered by radial ribs 49 that leave passages or apertures 51.

In this manner, the partial obstruction 48 permits passage of liquid from the port 22 to the cavity 16, but stops the partially inserted needle short of that cavity.

According to the illustrated preferred embodiment shown in FIG. 7, a dome 13'' is provided with a straight first passage 53 having a larger diameter than the needle 28 and a bottom portion 54 spaced from the cavity 16. The dome 13'' also has a second passage 55 extending between the first passage 53 and the cavity 16 in the same direction as the first passage. As shown in FIG. 7, the second passage may be laterally offset from the first passage.

As also shown in FIG. 7, the needle 28 is partially inserted into the first passage 53, but is stopped with the bottom portion 54 while an overflow and gas escape path 56 is preserved through the first passage 53 along the outside of the stopped, partially inserted needle 28.

The liquid 26 is then injected through the needle 28 and second passage 55 into the cavity 16 while overflow liquid and gas may escape through the path 56.

The remainder of the mode of operation and structure of the embodiments of FIGS. 5 to 7 are the same as for the embodiment of FIGS. 3 and 4 described in detail above.

Also, while specific embodiments have been herein shown and described, modifications and variations within the spirit and scope of the subject invention will become apparent or suggest themselves to those skilled in the art on the basis of the subject extensive disclosure.

I claim:

1. A method of filling a cavity and a port extending for a distance from said cavity with a liquid through a hypodermic needle longer than said distance, while permitting gas and excess liquid to escape, comprising in combination the steps of:

providing said port with a straight passage leading to said cavity;

partially inserting said needle into said straight passage of said port;

stopping said partially inserted needle by engagement inside said port short of said cavity while providing an overflow and gas escape path throughout said straight passage along the outside of said stopped partially inserted needle;

injecting liquid through said needle into said cavity while preserving said overflow and gas escape path; and withdrawing said needle from said port while continuing to inject liquid through said needle until said port is filled with said liquid.

2. A method as claimed in claim 1, wherein:

said straight passage is provided with a taper extending in the direction of said cavity and having a minor diameter smaller than the outside diameter of said hypodermic needle and with a straight path extending along said taper passage;

said partially inserted needle is stopped by engagement with a wall portion of said straight passage due to said taper short of said minor diameter.

3. A method as claimed in claim 1, wherein:

said straight passage is provided with a fluted taper having a minor diameter smaller than the outside diameter of said hypodermic needle; and said partially inserted needle is stopped by engagement with wall portions of said straight passage due to said taper short of said minor diameter.

4. A method as claimed in claim 1, wherein:

said straight passage is provided with a partial obstruction permitting passage of liquid from said port to said cavity but stopping said partially inserted needle short of said cavity.

5. A method of filling a cavity and a port extending for a distance from said cavity with a liquid through a hypodermic needle longer than said distance, while permitting gas and excess liquid to escape, comprising in combination the steps of:

providing said port with a straight first passage having a larger diameter than said needle and a bottom portion spaced from said cavity, and with a second passage extending between said first passage and said cavity in the same direction as said first passage;

partially inserting said needle into said first passage;

stopping said partially inserted needle with said bottom portion while providing an overflow and gas escape path through said first passage along the outside of said stopped partially inserted needle;

injecting liquid through said needle and second passage into said cavity while preserving said overflow and gas escape path; and withdrawing said needle from said port while continuing to inject liquid through said needle until said port is filled with said liquid.

6. A method as claimed in claim 5, wherein:

said second passage is laterally offset from said first passage.

7. An apparatus having a port and a cavity for receiving a liquid from a hypodermic needle through said port, comprising in combination:

a straight passage in said port leading to said cavity for receiving part of said needle;

means in said port for engaging said needle inside said port and stopping said needle short of said cavity; and means in said port for providing an overflow and gas escape path throughout said straight passage.

8. An apparatus as claimed in claim 7, wherein:

said needle engaging means include a partial obstruction in said port permitting passage of said liquid from said port to said cavity but stopping said needle short of said cavity.

9. An apparatus having a port and a cavity for receiving a liquid from a hypodermic needle through said port, comprising:

a tapered passage in said port extending in the direction of said cavity, having a minor diameter smaller than the outside diameter of said hypodermic needle whereby said needle is stopped short of said cavity, and having an overflow and gas escape path throughout said port.

10. An apparatus as claimed in claim 9, wherein:

said tapered passage is fluted.

11. An apparatus having a port and a cavity for receiving a liquid from a hypodermic needle through said port, comprising in combination:

a straight first passage in said port having a larger diameter than said needle and a bottom portion spaced from said cavity for stopping said needle short of said cavity; and a second passage extending between said first passage and said cavity in the same direction as said first passage.

12. An apparatus as claimed in claim 11, wherein:

said second passage is laterally offset from said first passage.

13. A dome for a pressure transducer having a port, a cavity for receiving a liquid from a hypodermic needle through said port, and an opening for a transduction of pressure variations relative to said cavity, comprising in combination:

an isolation membrane closing said opening for said liquid;

a straight passage in said port leading to said cavity for receiving part of said needle;

means in said port for engaging said needle inside said port and stopping said needle short of said cavity; and means in said port for providing an overflow and gas escape path throughout said straight passage.

14. An apparatus as claimed in claim 13, wherein:

said needle engaging means include a partial obstruction in said port permitting passage of said liquid from said port to said cavity but stopping said needle short of said cavity.

15. A dome for a pressure transducer having a port, a cavity for receiving a liquid from a hypodermic needle through said port, and an opening for a transduction of pressure variations relative to said cavity, comprising in combination:

an isolation membrane closing said opening for said liquid;

a tapered passage in said port extending in the direction of said cavity, having a minor diameter smaller than the outside diameter of said hypodermic needle whereby said needle is stopped short of said cavity, and having an overflow and gas escape path throughout said port.

16. An apparatus as claimed in claim 15, wherein:

said tapered passage is fluted.

17. A dome for a pressure transducer having a port, a cavity for receiving a liquid from a hypodermic needle through said port, and an opening for a transduction of pressure variations relative to said cavity, comprising in combination:
- an isolation membrane closing said opening for said liquid;
- a straight first passage in said port having a larger diameter than said needle and a bottom portion spaced from said cavity for stopping said needle short of said cavity; and
- a second passage extending between said first passage and said cavity in the same direction as said first passage.

18. An apparatus as claimed in claim 17, wherein:
said second passage is laterally offset from said first passage.

19. A method as claimed in claim 4, wherein:
said partial obstruction is centered by ribs leaving apertures for said passage of liquid from said port to said cavity.

20. An apparatus as claimed in claim 13, wherein:
said overflow and gas escape path providing means include means for providing said overflow and gas escape path along the outside of said stopped needle.

21. An apparatus as claimed in claim 14, including:
a second passage extending between said straight passage and said cavity past said partial obstruction in the same direction as said straight passage.

22. An apparatus as claimed in claim 14, wherein:
said partial obstruction is centered by ribs leaving passages for said liquid to said cavity.

23. An apparatus as claimed in claim 15, wherein:
said tapered passage has projecting ribs providing corresponding overflow and gas escape passages throughout said port along an outside of said stopped needle.

24. An apparatus having a port and a cavity for receiving a liquid through said port from a hypodermic needle having an outside, comprising in combination:
- a straight passage in said port leading to said cavity for receiving part of said needle;
- means in said port for engaging said needle inside said port and stopping said needle short of said cavity upon partial insertion of said needle; and
- means in said port for providing an overflow and gas escape path throughout said straight passage along the outside of the stopped, partially inserted needle.

25. An apparatus as claimed in claim 24, wherein:
said needle engaging means include a partial obstruction in said port permitting passage of said liquid from said port to said cavity but stopping said needle short of said cavity.

26. An apparatus as claimed in claim 25, including:
a second passage extending between said straight passage and said cavity past said partial obstruction in the same direction as said straight passage.

27. An apparatus as claimed in claim 24, wherein:
said partial obstruction is centered by radial ribs leaving passages for said liquid to said cavity.

28. An apparatus having a port and a cavity for receiving a liquid from a hypodermic needle through said port, comprising:
a tapered passage in said port extending in the direction of said cavity, having a minor diameter smaller than the outside diameter of said hypodermic needle whereby said needle is stopped short of said cavity, and having projecting ribs parallel to said tapered passage providing corresponding overflow and gas escape passages throughout said port along the outside of said stopped needle.

* * * * *